(12) United States Patent
Sarge et al.

(10) Patent No.: US 10,238,895 B2
(45) Date of Patent: Mar. 26, 2019

(54) ULTRASOUND CATHETER SYSTEM

(71) Applicant: FLOWCARDIA, INC., Sunnyvale, CA (US)

(72) Inventors: Jeff Sarge, Fremont, CA (US); Michael A. Summers, Santa Cruz, CA (US)

(73) Assignee: FLOWCARDIA, INC., Franklin Lakes, NJ (US)

( * ) Notice: Subject to any disclaimer, the term of this patent is extended or adjusted under 35 U.S.C. 154(b) by 743 days.

(21) Appl. No.: 14/415,126

(22) PCT Filed: Aug. 1, 2013

(86) PCT No.: PCT/US2013/053306
§ 371 (c)(1),
(2) Date: Jan. 15, 2015

(87) PCT Pub. No.: WO2014/022716
PCT Pub. Date: Feb. 6, 2014

(65) Prior Publication Data
US 2015/0190660 A1    Jul. 9, 2015

Related U.S. Application Data

(60) Provisional application No. 61/678,920, filed on Aug. 2, 2012.

(51) Int. Cl.
*A61N 7/02* (2006.01)
*A61B 17/22* (2006.01)
(Continued)

(52) U.S. Cl.
CPC ........ *A61N 7/022* (2013.01); *A61B 17/22012* (2013.01); *A61B 17/320016* (2013.01);
(Continued)

(58) Field of Classification Search
CPC ............ A61N 7/022; A61N 2007/0052; A61N 2007/0043; A61B 17/22012;
(Continued)

(56) References Cited

U.S. PATENT DOCUMENTS 4,535,759 A * 8/1985 Polk .................... A61N 7/00
601/2
4,979,952 A * 12/1990 Kubota ............ A61B 17/22012
310/316.01

(Continued)

OTHER PUBLICATIONS

Noone, D.: Experimental and Numerical Investigation of Wire Waveguides for Therapeutic Ultrasound Angioplasty. M.Eng. Dublin City University. 2008.

*Primary Examiner* — Phong Son H Dang

(57) ABSTRACT

An ultrasonic system operable at high drive frequencies and/or in pulsed operation is disclosed. The system may be used in a procedure to treat an occluded blood vessel. The system can be used to transmit ultrasonic energy from an ultrasonic transducer to a distal end of an ultrasonic transmission device. The ultrasonic device may operate at a resonant frequency. The resonant frequency can be determined prior to using the device and/or during use. The ultrasonic device may operate in a range of frequencies at or near resonance. Operational parameters including, for example, reflected vibrations, temperature, and/or user input can be used by the system to adjust the driving waveform.

6 Claims, 5 Drawing Sheets

(51) Int. Cl.
*A61B 17/32* (2006.01)
*A61B 17/00* (2006.01)
*A61N 7/00* (2006.01)

(52) U.S. Cl.
CPC ........... *A61B 17/320068* (2013.01); *A61B 2017/00106* (2013.01); *A61B 2017/00154* (2013.01); *A61B 2017/00172* (2013.01); *A61B 2017/00194* (2013.01); *A61B 2017/00292* (2013.01); *A61B 2017/00778* (2013.01); *A61B 2017/320056* (2013.01); *A61N 2007/0043* (2013.01); *A61N 2007/0052* (2013.01)

(58) Field of Classification Search
CPC .... A61B 17/320068; A61B 17/320016; A61B 2017/00154; A61B 2017/00194; A61B 2017/00778; A61B 2017/00106; A61B 2017/00172; A61B 2017/320056; A61B 2017/00292
See application file for complete search history.

(56) References Cited

U.S. PATENT DOCUMENTS

| | | | | |
|---|---|---|---|---|
| 5,131,393 | A * | 7/1992 | Ishiguro | A61B 8/12 600/445 |
| 5,312,328 | A * | 5/1994 | Nita | A61B 17/22012 604/22 |
| 5,324,255 | A * | 6/1994 | Passafaro | A61B 17/22012 128/898 |
| 5,329,927 | A * | 7/1994 | Gardineer | A61B 8/0833 600/439 |
| 5,391,144 | A * | 2/1995 | Sakurai | A61B 17/22012 601/3 |
| 5,449,370 | A * | 9/1995 | Vaitekunas | A61B 17/3476 604/22 |
| 5,542,917 | A * | 8/1996 | Nita | A61B 17/22012 601/3 |
| 5,627,365 | A * | 5/1997 | Chiba | B82Y 20/00 250/234 |
| 5,827,203 | A | 10/1998 | Nita | |
| 5,827,971 | A * | 10/1998 | Hale | G01H 9/00 73/657 |
| 6,004,335 | A * | 12/1999 | Vaitekunas | A61B 17/07207 227/180.1 |
| 6,007,514 | A | 12/1999 | Nita | |
| 6,066,135 | A * | 5/2000 | Honda | A61B 17/320068 601/2 |
| 6,427,118 | B1 | 7/2002 | Suzuki | |
| 6,500,141 | B1 * | 12/2002 | Irion | A61N 7/00 601/2 |
| 6,514,249 | B1 * | 2/2003 | Maguire | A61B 18/00 606/37 |
| 6,547,788 | B1 * | 4/2003 | Maguire | A61B 18/00 606/41 |
| 6,702,748 | B1 | 3/2004 | Nita et al. | |
| 6,855,123 | B2 | 2/2005 | Nita | |
| 6,942,620 | B2 | 9/2005 | Nita et al. | |
| 6,942,677 | B2 | 9/2005 | Nita et al. | |
| 7,137,963 | B2 | 11/2006 | Nita et al. | |
| 7,220,233 | B2 | 5/2007 | Nita et al. | |
| 7,297,131 | B2 | 11/2007 | Nita | |
| 7,335,180 | B2 | 2/2008 | Nita et al. | |
| 7,393,338 | B2 | 7/2008 | Nita | |
| 7,540,852 | B2 | 6/2009 | Nita et al. | |
| 7,604,608 | B2 | 10/2009 | Nita et al. | |
| 8,038,693 | B2 * | 10/2011 | Allen | A61B 17/320092 606/169 |
| 8,133,236 | B2 | 3/2012 | Nita | |
| 8,221,343 | B2 | 7/2012 | Nita et al. | |
| 8,226,566 | B2 | 7/2012 | Nita | |
| 8,246,643 | B2 | 8/2012 | Nita | |
| 8,978,478 | B2 * | 3/2015 | Ishioka | G01N 29/2418 73/602 |
| 9,284,984 | B2 | 3/2016 | Nita | |
| 2002/0189357 | A1 * | 12/2002 | Lai | B81C 99/005 73/584 |
| 2003/0060820 | A1 * | 3/2003 | Maguire | A61B 18/00 606/41 |
| 2004/0019349 | A1 * | 1/2004 | Fuinnaono | A61B 17/22012 606/41 |
| 2004/0024320 | A1 * | 2/2004 | Karasawa | B06B 1/0622 600/459 |
| 2004/0054367 | A1 * | 3/2004 | Jimenez, Jr. | A61N 7/02 606/41 |
| 2004/0193033 | A1 * | 9/2004 | Badehi | A61B 3/165 600/402 |
| 2005/0165388 | A1 * | 7/2005 | Bhola | A61B 18/1492 606/14 |
| 2005/0171527 | A1 * | 8/2005 | Bhola | A61B 18/1492 606/41 |
| 2006/0149169 | A1 * | 7/2006 | Nunomura | A61B 8/546 601/2 |
| 2007/0032749 | A1 * | 2/2007 | Overall | A61B 5/02444 600/595 |
| 2008/0006674 | A1 * | 1/2008 | Chan | H01L 24/78 228/1.1 |
| 2008/0139971 | A1 * | 6/2008 | Lockhart | A61N 7/00 601/2 |
| 2008/0208084 | A1 * | 8/2008 | Horzewski | A61N 7/00 601/2 |
| 2008/0294037 | A1 * | 11/2008 | Richter | A61B 8/0833 600/424 |
| 2010/0004558 | A1 * | 1/2010 | Frankhouser | A61B 10/025 600/567 |
| 2010/0023037 | A1 * | 1/2010 | Nita | A61B 17/22012 606/159 |
| 2010/0076454 | A1 * | 3/2010 | Bos | A61B 18/1492 606/130 |
| 2010/0121144 | A1 * | 5/2010 | Farhadi | A61B 1/00082 600/115 |
| 2010/0317973 | A1 * | 12/2010 | Nita | A61B 17/22012 600/467 |
| 2011/0105960 | A1 * | 5/2011 | Wallace | A61B 17/22012 601/2 |
| 2011/0137298 | A1 * | 6/2011 | Nguyen | A61N 7/022 606/1 |
| 2011/0237982 | A1 * | 9/2011 | Wallace | A61B 17/22012 601/2 |
| 2011/0313328 | A1 * | 12/2011 | Nita | A61N 7/022 601/2 |
| 2012/0010506 | A1 * | 1/2012 | Ullrich | A61B 1/00045 600/440 |
| 2012/0109021 | A1 * | 5/2012 | Hastings | A61N 7/00 601/2 |
| 2012/0330196 | A1 * | 12/2012 | Nita | A61N 7/022 601/2 |
| 2014/0243712 | A1 * | 8/2014 | Humayun | A61N 7/00 601/2 |
| 2015/0073357 | A1 * | 3/2015 | Bagwell | A61B 10/025 604/224 |
| 2015/0105621 | A1 * | 4/2015 | Farhadi | A61B 1/00082 600/115 |
| 2016/0328998 | A1 * | 11/2016 | Pedersen | G09B 23/28 |

* cited by examiner

ULTRASOUND CATHETER SYSTEM

PRIORITY

This application is a U.S. national stage application under 35 USC § 371 of International Application No. PCT/US2013/053306, filed Aug. 1, 2013, claiming priority to U.S. Provisional Application No. 61/678,920, filed Aug. 2, 2012, each of which is incorporated by reference in its entirety into this application.

BACKGROUND

Field of the Invention

This disclosure generally relates to a device, system, and method for generating, and transmitting ultrasonic vibrations to a treatment location. More particularly, the disclosure relates to an ultrasound device, system, and method for ablating obstructions within tubular anatomical structures such as blood vessels.

Description of the Related Art

There are many procedures and systems for treating vascular or venous obstructions that are occluded with atheroma, plaque, calcific material, and the like. Such obstructions are often referred to as vascular occlusions. Occlusions can be treated, for example, by a surgical bypass procedure or a catheter-based intervention such as angioplasty.

Ultrasound systems and devices have been proposed for use in ablating or removing obstructive material from blood vessels. Ultrasound catheters have been utilized to ablate various types of obstructions from blood vessels of humans and animals. Successful applications of ultrasound energy to smaller blood vessels, such as the coronary arteries, require the use of relatively small diameter ultrasound catheters which are sufficiently small and flexible to undergo transluminal advancement through the tortuous vasculature of the aortic arch and coronary tree. These ultrasound catheters incorporate a very small diameter ultrasound transmission member which extends through such catheters.

SUMMARY OF THE INVENTION

In some embodiments, a therapeutic ultrasonic vibration delivery system comprises an elongate ultrasound transmission device having a distal end and a proximal end and an ultrasonic driver coupled to the proximal end of the transmission device and configured to drive the transmission device such that the distal end of the transmission device vibrates at a frequency of at least 18 kHz. In some aspects, the transmission device comprises an ultrasound transmission member disposed within a lumen of a catheter body. The ultrasonic driver may include a signal generator coupled to an ultrasound transducer. The ultrasonic driver may be configured to deliver pulses of ultrasonic vibration. The ultrasonic driver may be configured to drive the transmission device at a resonant frequency of the transmission device.

In some embodiments, a method of recanalizing a lumen of a vessel comprises positioning an ultrasonic device having a distal end in a first position within the lumen of the occluded vessel, transmitting an ultrasonic vibration of at least 18 kHz though the ultrasonic device, and advancing the distal end through the occluded vessel to recanalize the vessel. The positioning step may include snaking the device through a tortuous path. In some aspects, the transmitted vibration is about 40 kHz.

In some embodiments, a therapeutic ultrasonic vibration delivery system comprises an elongate ultrasound transmission device having a distal end and a proximal end, and an ultrasonic driver coupled to the proximal end of the transmission device and configured to drive the transmission device in a pulsed mode. The pulsed mode may drive the device with a duty cycle of about 50% which may be optimized for ablating a particular substrate.

In some embodiments, a method of recanalizing a lumen of a vessel comprises positioning an ultrasonic device having a distal end in a first position within the lumen of the vessel, transmitting pulsed ultrasonic vibrations though the ultrasonic device to the distal end, and advancing the distal end through the vessel to recanalize the vessel. The pulsed ultrasonic vibrations can increase the displacement of the distal end of the ultrasonic device.

In some embodiments, a therapeutic ultrasonic vibration delivery system comprises an elongate ultrasound transmission device having a distal end and a proximal end and an ultrasonic driver coupled to the proximal end of the transmission device and configured to drive the transmission device through a range of ultrasonic frequencies. The ultrasonic driver may be configured to drive the transmission device by sweeping continuously through a range of ultrasonic frequencies. The range of ultrasonic frequencies may be between about 18 kHz and 22 kHz and may include at least one resonant frequency of the transmission device.

In some embodiments, a method of recanalizing a lumen of a vessel comprises positioning an ultrasonic device having a distal end in a first position within the lumen of the vessel, transmitting a range of ultrasonic vibrations though the ultrasonic device to the distal end, and advancing the distal end through the lumen of the vessel to recanalize the vessel.

In some embodiments, a therapeutic ultrasonic vibration delivery system comprises an elongate ultrasound transmission device having a distal end and a proximal end, a detector configured to determine a resonant frequency of the ultrasound transmission device, and an ultrasonic driver coupled to the proximal end of the transmission device and configured to drive the ultrasound transmission device at the resonant frequency. The resonant frequency may be determined by using a measurement pulse transmitted through the transmission device.

In some embodiments, a therapeutic ultrasonic vibration delivery system comprises an elongate ultrasound transmission device having a distal end and a proximal end, an ultrasonic driver coupled to the proximal end of the transmission device and configured to transmit ultrasonic vibrations through the transmission device, and a detector coupled to the transmission device and configured to determine the displacement of the distal end of the transmission device. The detector may be configured to determine the displacement of the distal end of the transmission device at least in part by detecting a reflected vibration.

In some embodiments, a method of controlling the frequency of vibration applied to an ultrasound device, comprises applying a vibration having an ultrasonic frequency to the ultrasound device, detecting a reflected vibration, and applying a second vibration based at least in part on the detected vibration.

In some embodiments, a method of recanalizing a lumen of a vessel, comprises positioning an ultrasonic device having a distal end in a first position within the lumen of the vessel, determining a resonant frequency of an ultrasound transmission device, vibrating the ultrasound transmission device at the resonant frequency, and advancing the distal end through the occluded vessel to recanalize the vessel. The determining step may occur when the distal end is within the lumen of the occluded vessel.

In some embodiments, a therapeutic ultrasonic vibration delivery system comprises an elongate ultrasound transmission device having a distal end and a proximal end, and an ultrasonic driver coupled to the proximal end of the transmission device and configured to drive the transmission device such that the distal end of the transmission device vibrates at a frequency of at least 20 kHz. The ultrasonic driver may be configured to deliver pulses of ultrasonic vibrations. The pulsed delivery may include a pulse repetition frequency between about 5 milliseconds and 30 milliseconds. In some embodiments, the pulsed deliver comprises delivering a first vibration for a first time period and delivering as second vibration for a second time period. In some embodiments, the pulsed delivery comprises applying a first vibration for a first time period, and then turning the driver off for a second time period, followed by applying, a third vibration for a third time period. In some embodiments, a method of driving a therapeutic ultrasound device comprises determining a resonant frequency of an ultrasound transmission device and vibrating the ultrasound transmission device at the resonant frequency.

DETAILED DESCRIPTION OF CERTAIN PREFERRED EMBODIMENTS

The following description and the accompanying figures describe and show the preferred embodiments as well as demonstrate several possible configurations for a device, system, and method. The illustrations are not intended to limit the disclosed aspects and features of the invention to the specified embodiments or to usage only with the illustrated device. Those of skill in the art will recognize that the disclosed aspects and features of the invention are not limited to any particular embodiment of a device, which may include one or more of the inventive aspects and features described herein.

To assist in the description of these components of the device, the following coordinate terms are used A "longitudinal axis" is generally parallel to a portion of the device as well as parallel to the axis of a vessel through which the device can travel. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the device, and therefore is substantially synonymous with the term "longitudinal" as used herein. Also, the terms "proximal" and "distal," which are used to describe the present system, are used consistently with the description of the exemplary applications (i.e., the illustrative examples of the use applications). Thus, proximal and distal are also used in reference to the respective ends of the device.

To facilitate a complete understanding of the embodiments, the remainder of the detailed description describes the system with reference to the Figures; Wherein like elements among the embodiments are referenced with like numerals throughout the following description.

Figure 1:
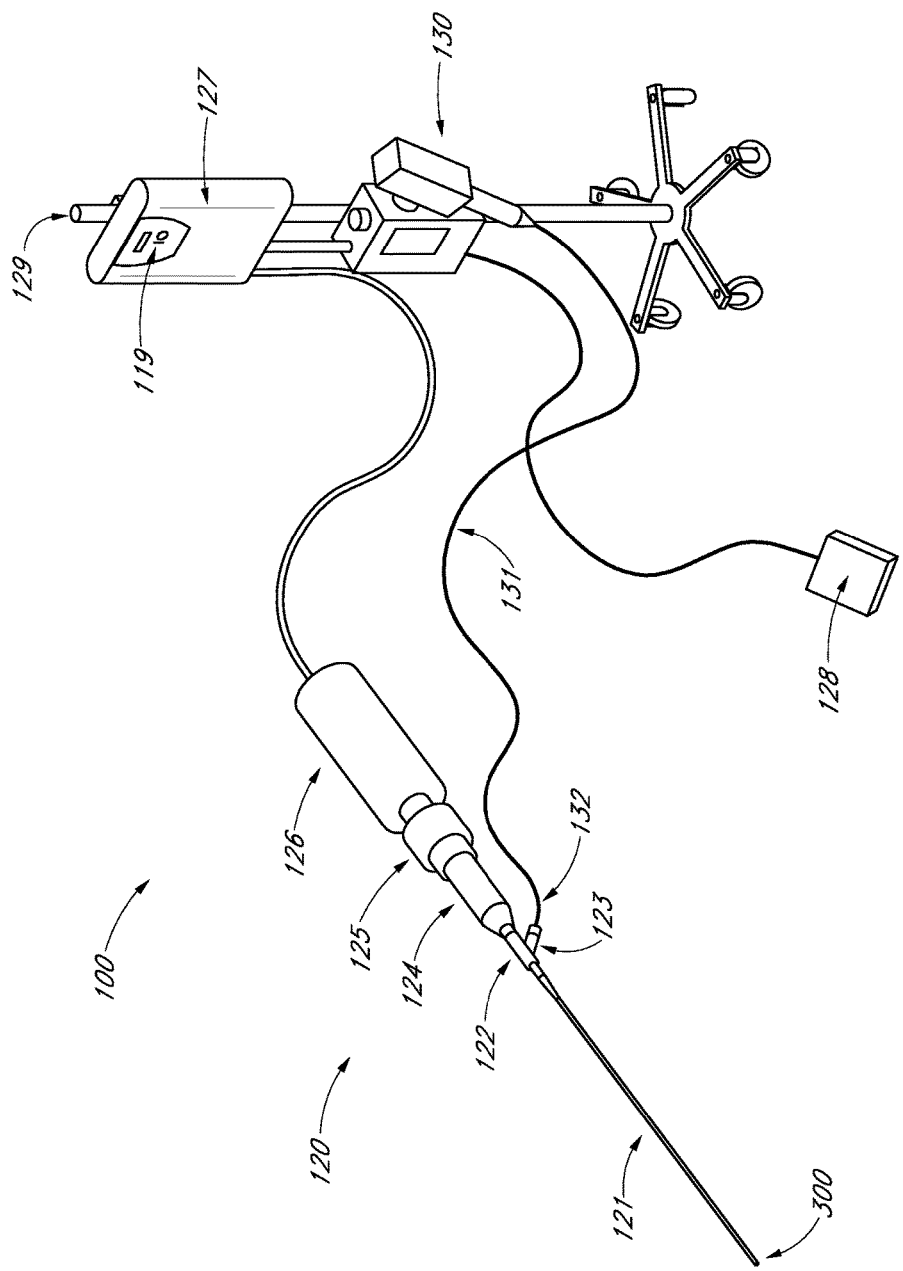
FIG. 1 is a perspective view of an ultrasound system according to a preferred embodiment of the present invention.

FIG. 1 shows an example of a perspective view of an ultrasound system 100 that can be used to ablate vascular occlusions. The ultrasound system 100 includes an ultrasound device 120 which is releasably coupled to an ultrasound transducer 126. The ultrasound transducer 126 is electrically coupled to a signal generator 127.

The ultrasound device 120 may include an elongate body having a proximal portion 122 and a distal portion 121. The ultrasound device 120 may be an ultrasonic energy delivery member, or a catheter having at least one lumen extending longitudinally with an ultrasound transmission member extending therethrough.

The ultrasound device 120 may also include a Y-connector 123 that is operatively coupled to the ultrasound transducer 126. For example, the Y-connector 123 may be coupled to the ultrasound transducer 126 by way of a device knob 124 and a slide collar 125. The ultrasound transducer 126 may be connected to a signal generator 127, which may be coupled to a foot actuated on-off switch 128. The signal generator 127 can be supported by an IV pole 129. When the on-off switch 128 is depressed, the signal generator 127 can send an electrical signal to the ultrasound transducer 126, which converts the electrical signal to ultrasound energy. Such ultrasound energy can subsequently pass through the ultrasound device 120 and be delivered to the distal portion 121. A conventional guidewire may be utilized in conjunction with the device 120. The distal portion 121 may comprise a distal end 300.

The frontal portion of the Y-connector 123 may be connected to the proximal end 122 of the ultrasound device 120 using techniques that are well-known in the art. An injection pump 130 or IV bag or syringe may be connected, by way of an infusion tube 131, to an infusion port or sidearm 132 of the Y-connector 123. The injection pump 130 can be used to infuse coolant fluid into and/or through the device 120. Such flow of coolant fluid may be utilized to prevent overheating of the ultrasound transmission member and may serve to bathe the outer surface of the ultrasound transmission member, thereby providing for an equilibration of temperature between the coolant, fluid and the ultrasound transmission member. The temperature and/or flow rate of coolant fluid may be adjusted to provide adequate cooling and/or other temperature control of the ultrasound transmission member. The irrigation fluid can include a pharmacological agent and/or microbubbles. In addition to the foregoing, the injection pump 130 or syringe may be utilized to infuse a radiographic contrast medium into the device 120 for purposes of imaging. Examples of iodinated radiographic contrast media which may be selectively infused into the ultrasonic device 120 via the injection pump 130 are commercially available as Angiovist 370 from Berlex Labs, Wayne, N.J. and Hexabrix from Malinkrodt, St, Louis. Mo.

Generally, the ultrasonic device 120 may include any suitable number of side-arms or ports for passage of a guidewire, application of suction, infusing and/or withdrawing irrigation fluid, dye and/or the like, or any other suitable ports or connections. Also, the device may be used with any suitable ultrasound transducer 126, signal generator 127, coupling device(s) and/or the like. Therefore, the exemplary embodiment shown in FIG. 1 and any following descriptions of proximal apparatus or systems for use with ultrasound devices 120 should not be interpreted to limit the scope of the present invention as defined in the appended claims.

Figure 2:
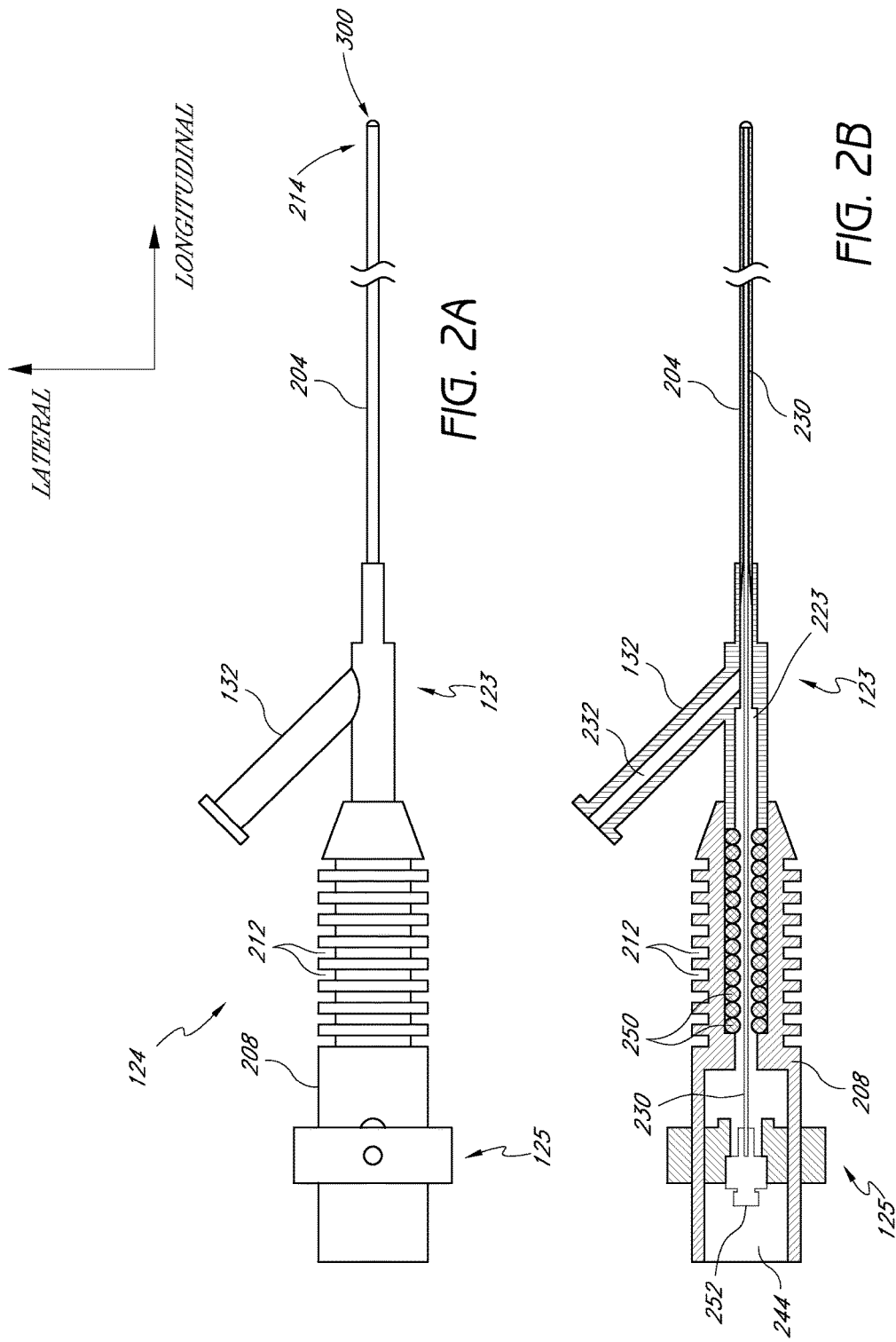
FIG. 2A is a side view of the ultrasound device shown in FIG. 1.
FIG. 2B is a cross-sectional side view of the ultrasound device shown in FIG. 2A.

FIG. 2A is a side view of the ultrasound device 120 shown in FIG. 1. As illustrated, the distal portion of the Y-connector 123 is coupled to a catheter body 204. The ultrasound transmission member 230 can pass through the device knob 124, Y-connector 123, and catheter body 204, and abut at least a portion of the distal head of the catheter body 204. In some embodiments, the ultrasound transmission member 230 can emerge through the distal end of the catheter body 204 rather than abut at the distal end of the catheter body 204. In some embodiments, the distal tip of the ultrasound transmission member 230 is secured directly to the distal end of the catheter body 204.

Continuing with FIG. 2A, the device knob 124 includes a proximal housing 208. The housing 208 may include one or more surface features 212 for increasing the outer surface area of housing 208. Increased surface area can enhance the ability of housing 208 to dissipate heat generated by ultrasound transmission member 230. Surface features 212 may be of any suitable size or shape and can include, for example, ridges, jags, undulations, grooves or the like. Any suitable number of surface features 212 may be used. Additionally, the housing 208 may be made of one or more heat dissipating materials, such as aluminum, stainless steel, any other conductive metal(s), or any suitable non-metallic conductive material.

The catheter body 204 may be a generally flexible, tubular, elongate member, having any suitable diameter and length for reaching a vascular occlusion. In some embodiments, for example, the catheter body 204 has a length in the range of about 100-200 cm. In one embodiment, the catheter body 204 has an outer diameter in the range of about 0.5-5.0 mm. In other embodiments, for use in relatively small vessels for example, the catheter body 204 may have an outer diameter in the range of about 0.25-2.5 mm. However, any other suitable length or diameter may be used without departing from the scope of the present invention. Examples of catheter bodies similar to those which may be used in the present invention are described in U.S. Pat. Nos. 5,267,954 and 5,989,208, which are herein incorporated by reference in their entireties. In one embodiment, the catheter body 204 is formed of a flexible polymeric material such as nylon (Pebax™) manufactured by Atochimie, Cour be Voie, Hauts Ye-Sine, France. The catheter body 204 can insulate the ultrasound transmission member 230 and prevent an operator's hands from contacting the ultrasound transmission member 230 during use of the device.

In some embodiments, the catheter body 204 includes one or more radiopaque markers located at a distal portion 214 of the catheter body 204. In one embodiment, the distal portion 214 is made of a radiopaque polymer or similar materials known in the art. The radiopaque materials can increase visibility under fluoroscopy and facilitate the correct positioning of the device. In another embodiment, intravascular ultrasound or other imaging modalities may be employed. Alternate imaging techniques may include Optical Coherence Tomography (OCT) and/or magnetic fields (Stereotaxis Inc.) to further facilitate positioning of the distal portion 214 within a patient.

FIG. 2B shows a cross-sectional view of the ultrasound device 120 shown in FIG. 2A. As depicted, the housing 208 can include an inner cavity 244. Disposed within the cavity 244 is a some connector 252. The ultrasound transmission member 230 extends in a distal direction from the some connector 252 and through the cavity 244.

The inner cavity 244 may include one or more vibration absorption members 250. The vibration absorption members 250 can increase the ease of use by decreasing vibrations transmitted from the ultrasound transmission member 230 through the housing 208. The some connector 252 can facilitate the coupling, of the ultrasound transmission member 230 to an ultrasound transducer device 126. The ultrasound transmission member 230 may extend distally from the sonic connector 252, through the inner cavity 244, Y-connector 123 and catheter body 204.

Continuing with FIG. 2B, the sidearm 132 may include a lumen 232 in fluid communication with a lumen 223 in the Y-connector 123. The lumen 223 in the Y-connector 123 can be in fluid communication with a lumen extending through the catheter body 204. Thus, fluid introduced into the sidearm 132 may flow into and through the catheter body 204 and contact the ultrasound transmission member 230. The fluid may flow out of the catheter body 204 through apertures in the distal portions or through any other suitable apertures or openings, such as apertures located in the catheter body 204 itself.

Any suitable fluid may be passed through the sidearm 132 and catheter body 204. Suitable fluids include, for example, refrigerated fluids, lubricious fluids, saline, saturated saline, super-saturated saline, contrast/saline mixtures, or the like. Cooling and/or lubricating the ultrasound transmission member 230 may reduce friction and/or wear and tear of the ultrasound transmission member 230, thus prolonging the ultrasound transmission member's useful life and enhancing overall performance.

As shown in FIG. 2B, the catheter body 204 defines a main lumen. However, the catheter body 204 can comprise an elongate tube with one or more lumens extending longitudinally therethrough. With continued reference to FIG. 2A, extending longitudinally through the main lumen of the catheter body 204 is an elongate ultrasound transmission member 230 having a proximal end. The proximal end may be removably connectable to an ultrasound transducer via the sonic connector 252 such that ultrasound energy can pass through the ultrasound transmission member 230 from the proximal end to the distal portion of the ultrasound transmission member 230.

In some embodiments, the ultrasound transmission member 230, wire, or wave guide extends longitudinally through a lumen of the catheter body 204. Ultrasonic energy can travel through the ultrasound transmission member 230 from an ultrasound transducer 126 connected to the proximal end of housing 208 to the distal portion of the device. The ultrasound transmission member 230 may operate at frequencies between about 18 kHz to about 150 kHz. In one embodiment, the frequency of vibration is about 20 kHz. In some embodiments, the ultrasound transmission member 230 operates at frequencies between about 40 kHz to about 150 kHz. In one embodiment, the frequency of vibration is greater than about 40 kHz. The ultrasound transmission member 230 may operate in continuous mode, pulse mode, or combination of both.

The ultrasound transmission member 230 may be formed of any material capable of effectively transmitting ultrasonic energy from the ultrasound transducer to the distal end of the ultrasound transmission member 230. These materials include, but are not limited to, metals such as pure titanium or aluminum, or titanium or aluminum alloys, such as NiTi.

The ultrasound transmission member 230 may include one or more tapered regions and/or steps. The tapered regions and steps may increase and/or decrease in width or diameter along the length of the ultrasound transmission member 230 in the distal direction. In one embodiment, the ultrasound transmission member 230 includes at least one portion tapered in a direction extending distally from the proximal end. In another embodiment, the ultrasound transmission member 230 is continuously tapered in a direction extending distally from the proximal end. In one embodiment, the ultrasound transmission member 230 tapers in diameter from about 800 μm proximally, to about 200 μm distally.

Additional details of ultrasound systems and devices that include ultrasound transmission members (and their distal tips), catheter bodies (and their distal tips), ultrasound transducers, sonic connectors, and their connections to ultrasound devices are disclosed, for example, in U.S. Pat. Nos. 5,827,203, 6,007,514, 6,427,118; 6,702,748; 6,855,123; 6,942,620; 6,942,677; 7,137,963; 7,220,233; 7,297,131; 7,335,180; 7,393,338; 7,540,852, 7,604,608, 8,133,236 and in U.S. Pat. App. Pub. Nos. 2006/0161098, 2007/0239027, 2008/0108937, 2008/0287804, 2010/0317973, the disclosures of which are hereby incorporated by reference in their entireties.

Returning to FIG. 1, the signal generator 127 can send electrical signals to the ultrasound transducer 126. The ultrasound transducer 126 can then convert the electrical signals to ultrasonic vibrations. The ultrasonic vibrations can then be transmitted through the ultrasound transmission member and delivered to a treatment location. A treatment location can be an area of a vessel and/or vessel wall that has stenosis or restenosis. Vessels can include veins and arteries. The methods and devices described herein can also be applied to other body lumens and organs, for example, biliary ducts.

In use, the system must provide sufficient ultrasonic vibration to the treatment location in order to provide a therapeutic benefit. For example, when used to open or recanalize a fully or partially blocked vessel, or lumen, the system 100 must provide enough vibration to penetrate and/or ablate the blockage. Often, after treating an occluded vessel, a stent can be placed in the vessel to enlarge and/or support the vessel. Various system parameters can be adjusted and optimized as will be explained below.

In some embodiments, the power delivery can be optimized to deliver ultrasonic vibrations to a treatment site at the end of a tortuous path. For example, the signal generator 127, ultrasound transducer 126, and/or any other suitable component can be configured such that the ultrasound device 120 can penetrate and/or ablate occlusions when the ultrasound device 120 is threaded through tortuous paths. That is to say, when the ultrasound device 120 is threaded through the vasculature to a treatment location, the ultrasound device 120 must bend. The more tortuous the path through the vasculature (for instance, during coronary applications), the more bends the ultrasound device 120 must undertake. Higher frequency (shorter wavelength) ultrasonic energy travels easier around bends than lower frequency (longer wavelength) ultrasonic energy. Because higher frequency ultrasonic energy (for example ≥40 kHz) travels easier around bends than lower frequency ultrasonic energy, less energy is lost when traveling through the ultrasonic device and more energy is delivered to the treatment location. Accordingly, the system disclosed herein can include a signal generator 127 and/or ultrasound transducer 126 configured to drive the ultrasound device 120 at frequencies greater than or equal to about 18 kHz. In some embodiments, the signal generator 127 is configured to provide drive frequencies from about 18 kHz to about 150 kHz. In some embodiments, the ultrasound transducer 126 is configured to deliver ultrasonic vibrations from about 18 kHz to about 150 kHz through the ultrasonic device. In some embodiments, mass of the ultrasound transducer 126 is reduced in order to run at higher drive frequencies, for example, above 40 kHz.

In some embodiments, power delivery is optimized by delivering pulsed ultrasonic vibrations to a treatment location. With reference to FIG. 1, in some embodiments, the signal generator 127, ultrasound transducer 126, and/or any other suitable component includes one or more actuators 119 for switching between two or more modes or types of ultrasound energy transmission through the ultrasonic device 120. Actuator 119 may be used, for example, to switch between the transmission of pulsed ultrasound signal and a continuous ultrasound signal. Providing two or more different types of ultrasound signal may enhance disruption of a vascular occlusion, and in various embodiments, switching between types of signals may be performed in any order desired, as many times as desired, without stopping the transmission of ultrasound energy to make the switch and/or the like. Although actuator 119 is illustrated on the signal generator 127 in FIG. 1, it may be given any other location and configuration. Some embodiments do not include an actuator; rather the signal generator 127 and/or the ultrasound transducer 126 are configured to operate in only a pulsed mode or in only a continuous mode or configured to operate in a self-switching mode based at least in part upon the distal environment and/or the reflected energy.

In a pulsed operation, parameters such as the number of pulses occurring in a given time period (pulse frequency), the time from the beginning of one pulse to the beginning of the next (pulse period), and the time it takes for one pulse to occur (pulse duration) can all be adjusted and selected. For example, in certain embodiments the time between pulses is 5 milliseconds which results in much faster "drilling." The signal generator 127 can further be operated at a higher frequency, such as 135 kHz.

In some embodiments, the signal generator 127, ultrasound transducer 126, and/or any other suitable component may be configured to provide a pulsed ultrasound signal. The pulsed ultrasound signal can have any suitable duty cycle. In some embodiments, the duty cycle can be in the range of approximately 30-70% (i.e., off 70-30%) or any other suitable range. The frequency of the duty cycle can be any suitable frequency and can be adjusted prior to use or during use. In other words, the length of time that the device is on or off in a given period can be manipulated and optimized. For example, the duty cycle can be optimized for particular materials that the device may encounter. In particular, the device can penetrate harder materials in pulsed operation. Thus, the applied wave form can be altered and/or optimized.

In some embodiments, when ultrasound energy travels through the ultrasound device, there is an initial period of time during which the distal tip of the ultrasound device vibrates in a more random and aggressive manner than during later time periods in the same activation cycle in part because the tip vibrations settle into a steady state. These initial vibrations may provide the greatest erosion performance against harder substrates. Therefore, by pulsing the energy on and off rapidly, this start-up energy can be supplied many more times in a given time period. For example, in some embodiments, a 50% duty cycle with 30 ms on and 30 ms off pulses can provide one start-up burst every 60 ms. A 50% duty cycle with 10 ms on and 10 ms off can provide three start-up bursts every 60 ms. Furthermore, a 33% duty cycle with 10 ms on and 20 ms off can provide two start-up bursts every 60 ms. In some embodiments, the ultrasound device can operate at lower temperature and fatigue after a longer time period, at least in part because of the reduced duty cycle.

The signal generator 127 can be configured to provide square wave signals or sinusoidal wave signals to the ultrasound transducer 126. In some embodiments, the signal generator 127 is configured to provide any programed wave shape. In one embodiment for example, the signal generator 127 is configured to provide one or more input signals to the ultrasound transducer 126 separated by time gaps when no signal is provided. The pulse period, pulse frequency, and pulse duration can be selected and optimized.

The pulsed operation of the devices disclosed herein can increase displacement of the distal tip 300 and can cause the distal tip 300 to move erratically. This increased displacement and erratic movement enhances the ability of the distal tip 300 to penetrate hard and/or dense materials. In other words, operating the device in a pulsed ultrasonic mode can increase the effectiveness of the device by increasing movement of the distal end of the ultrasonic device to, for example, ablate the desired material.

Figure 4:
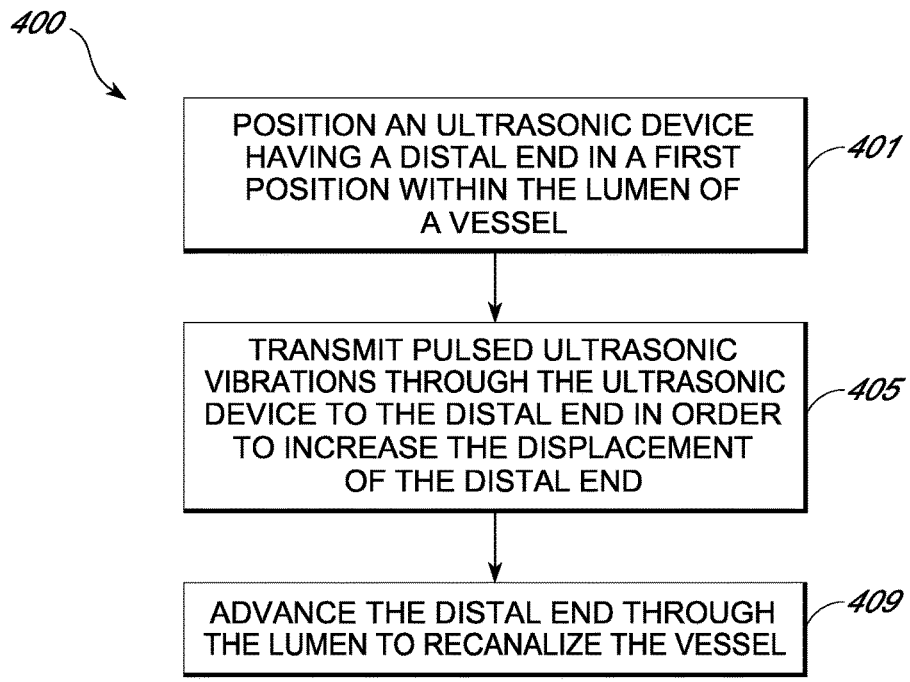
FIGS. 4-6 are flow diagrams illustrating methods of recanalizing vessels according to some embodiments.

FIG. 4 is a flow diagram illustrating a method 400 of recanalizing a vessel using of pulsed ultrasonic vibrations. The method can begin at block 401 by positioning an ultrasonic device having a distal end in a first position within the lumen of a vessel. The first position may be proximal to an occlusion. The occlusion may be a partial or total occlusion. The ultrasonic device may include one or more or the components described above. The method 400 can continue at block 405 by transmitting pulsed ultrasonic vibrations to the distal end of the ultrasonic device. The pulsed ultrasonic vibrations can increase the displacement of the distal tip and improve performance of the ultrasonic device by ablating the occlusion faster and to a greater extent than previous devices. In some embodiments, the pulsed vibrations include transmitting a first frequency for a first time period, followed by transmitting a second frequency for a second time period. In some embodiments, the vibrations are applied for a first time period followed by a second time period when no vibrations are applied followed by a third time period where vibrations are again applied. The vibrating distal end of the device may be advancing through the occlusion while ultrasonic vibrations are applied to the proximal can of the device. The method 400 can end at block 409 by advancing the distal end to through the vessel to recanalize the vessel.

With reference to FIG. 1, in some embodiments power delivery is optimized by configuring the ultrasound system 100 to operate at the resonant frequency of the ultrasound device 120 for at least a period of time during use. In general, when the ultrasonic frequency applied to the ultrasound device 120 matches the natural frequency of the ultrasound device 120 it will begin to resonate. The effectiveness of the ultrasound device 120 is enhanced at resonance because the amplitude with which the distal end 300 of the ultrasound device moves 120 is maximized at resonance. As such, the distal end 300 can penetrate material and/or tissue more effectively during resonant vibration because the distal end 300 moves back and forth across the greatest distance and more energy is imparted against the blockage.

In some embodiments, the signal generator 127, ultrasound transducer 126, and/or any other suitable component can be configured to operate at the resonant frequency of a particular ultrasound device 120 during use. For example, a particular ultrasound device 120 has a particular resonant frequency associated with the device 120. The resonant frequency can depend on the unique characteristics of the ultrasound device 120 (for example, the particular ultrasound transmission member and/or catheter body used and/or the particular configuration of the distal end). Factors such as length, thickness, and material of the ultrasound transmission member and/or catheter body can also affect the resonant frequency. Thus, prior to use, the resonant frequency for a particular ultrasound device 120 can be determined. In general, the resonant frequency can be expected to be similar for the particular ultrasound device 120 within manufacturing tolerances. However, in some embodiments, the resonant frequency of each particular ultrasound device can be determined prior to use.

Furthermore, during use, the resonant frequency of the particular ultrasound device 120 changes because of factors such as the amount or tortuosity the ultrasound device 120 and/or components thereof is subjected to, the temperature, and the load on the distal end 300. These changing factors during use of the ultrasound device 120 can change the resonant frequency of the device by, for example, about +/−10%.

In some embodiments, the ultrasound system 100 is configured such that the ultrasound device 120 operates at resonant frequency for at least a period of time by continually sweeping across a range of applied ultrasonic frequencies during operation. For example, the signal generator 127, ultrasound transducer 126, and/or any other suitable component can be configured to apply ultrasound vibration to the ultrasound device 120 in a back and forth sweeping manner through a range of frequencies. By sweeping across a given range of frequencies, the ultrasound device 120 is likely to achieve resonance for at least a portion of time during the sweep.

Figure 5:
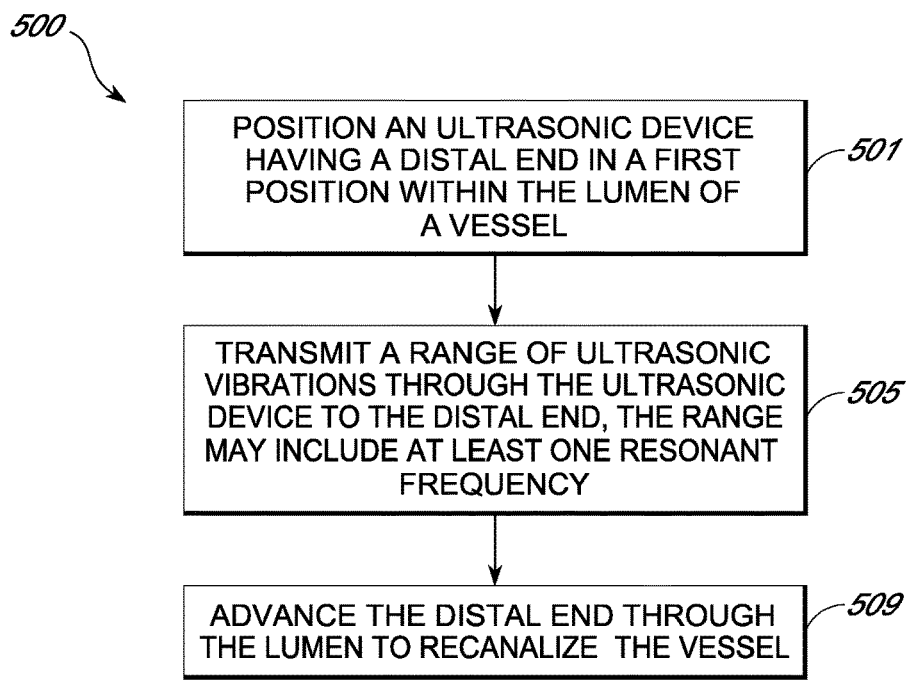

FIG. 5 is a flow diagram illustrating a method 500 of recanalizing a vessel by applying a range of ultrasonic vibrations to an ultrasound transmission device. The method can begin at block 501 by positioning the ultrasonic device having a distal end in a first position within the lumen of a vessel. The first position may be proximal to a partial or total occlusion. The distal end of the ultrasonic device may contact the occlusion. The ultrasonic device may include one or more or the components described above. The method 500 can continue at block 505 by transmitting a range of ultrasonic vibrations to the distal end of the ultrasonic device. The range of ultrasonic vibrations may be between 1 kHz and 10 MHz. In some embodiments, the range is between 18 kHz and 22 kHz and/or includes at least one resonant frequency of the transmission device. By delivering a range of ultrasonic vibrations the displacement of the distal tip may be increased, improving performance of the ultrasonic device by ablating the occlusion faster and to a greater extent than previous devices. The method 500 can end at block 509 by advancing the distal end through the vessel to recanalize the vessel.

In some embodiments, prior to using the device, the resonant frequency for a particular ultrasound device 120 design can be determined. The system 100 can then be configured to sweep across this resonant frequency in a range of about +/−10% of the known resonant frequency. In one embodiment, for example, the vibration applied to the ultrasound device 120 sweeps continually back and forth between the range of 18 kHz and 22 kHz. In another embodiment, the vibration applied to the ultrasound device 120 sweeps continually from 18 kHz to 22 kHz and then repeats the sweep starting again at 18 kHz. The range of ultrasonic frequencies may be between about 1 kHz and 10 MHz. In some embodiments, the range of ultrasonic frequencies is between about 10 kHz and 50 kHz. In one embodiment, the applied ultrasonic frequency on the ultrasound device 120 is increased and/or decreased in discrete incremental steps though a given frequency range. For example, the applied frequency can start at 18 kHz and increase in 0.1 kHz increments until 22 kHz is reached and then decrease in 0.1 kHz increments until 18 kHz is reached. The sweep interval, or the period of time it takes to sweep through a given frequency range, can also be adjusted and optimized.

The materials for the ultrasound device 120 may be selected to facilitate the penetration and/or ablation by the ultrasound device 120. These different materials can have different physical properties such as hardness or density. Different frequencies of vibration may be preferred over others depending on the physical properties of such materials. In some embodiments, the device is optimized and/or adjusted to penetrate hard plaques and/or rigid deposits and in other embodiments, the device is optimized and/or adjusted to penetrate soft tissues. In some embodiments, the device is optimized and/or adjusted to penetrate fibrous tissue. As such, configuring the system 100 to sweep through a range of frequencies can also increase the likelihood that the ultrasound device 120 will vibrate at the particular frequency and/or wave form best suited for removing the particular material.

In some embodiments, the signal generator 127, ultrasound transducer 126, and/or any other suitable component can be configured to determine the resonant frequency of a particular ultrasound device 120 during use. Once the resonant frequency is determined, the system can then be configured to operate at resonance during use. As discussed above, the resonant frequency for the ultrasound device 120 can change during use due to factors such as, for example, the amount of tortuosity the ultrasound device 120 is subjected to, the temperature, and the load on the distal end 300. The resonant frequency of the system may also change when the transducer changes temperature. In one embodiment, the resonant frequency during use of the device is determined by configuring the signal generator 127, ultrasound transducer 126, and/or any other suitable component to be paused briefly during use. In other words, the ultrasound transducer 126 can momentarily stop transmitting vibrations through the ultrasound device 120. Such stoppages may be intermittent and/or periodic.

While the transmission of vibrations is momentarily stopped, the ultrasound transducer 126 and/or other suitable component can send a measurement pulse through the ultrasound device 120. The measurement pulse can then be used to determine the actual resonance of the ultrasound device 120. The signal generator 127, ultrasound transducer 126, and/or any other suitable component can then be adjusted to deliver this resonant frequency through the ultrasound device 120. In some embodiments, this measurement and adjustment is done automatically. At a later point in time, the transmission of vibrations can again be momentarily stopped, a measurement signal can be sent through the device, the resonant frequency can be determined, and the system can be adjusted to deliver this resonant frequency. As such, in some embodiments, the resonant frequency of the ultrasound device 120 can be determined and the device adjusted to operate at or near resonance during a procedure.

Figure 3:
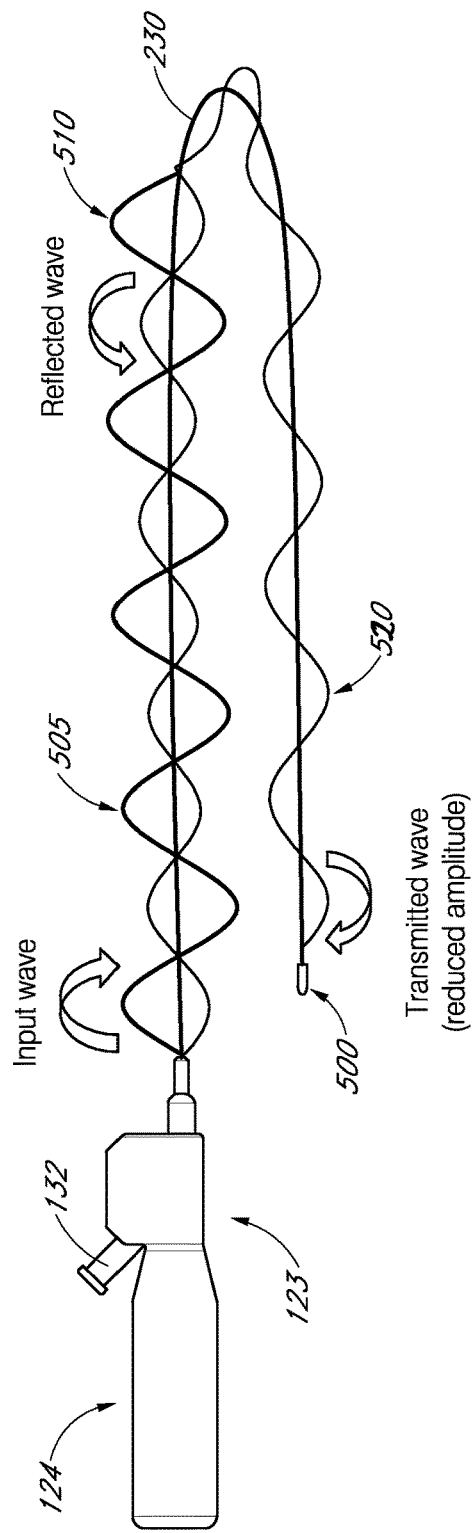
FIG. 3 is a schematical side view of the ultrasound device in one mode of operation.

In some embodiments, the ultrasound system 100 is configured such that the displacement of the distal end 300 of the ultrasound device 120 is measured and controlled during use. For example, as shown in FIG. 3, when an ultrasonic wave is transmitted from the ultrasound transducer through the ultrasound transmission member 230 (input wave 505), a portion of the transmitted wave is reflected (reflected wave 510) and a portion of the wave reaches the distal head 500 (transmitted wave 520). Waves can be reflected, as illustrated for example in FIG. 3, at bends in the ultrasound transmission member 230.

The ultrasound transducer 126 or another transducer or device can be configured to detect and measure the amplitude of the reflected wave 510. The difference in amplitude between the input wave 505 and the reflected wave 510 can be used at least in part to determine the amplitude of the transmitted wave 520. As such, the ultrasound system 100 can determine the amplitude of the transmitted wave 520 by comparing the values of the amplitude of the transmitted wave 520 and the amplitude of the reflected wave 510. The device can adjust the amplitude of the input wave based at least in part on amplitude of the transmitted wave 520. For example, the input wave can be adjusted so as to keep the amplitude of the transmitted wave 520 relatively constant. In other words, the displacement of the distal end of the ultrasonic device can be monitored in real time and the ultrasonic drive system can be continually adjusted so that the displacement of the distal tip can be controlled.

The following illustrates an exemplary method of using the ultrasonic system 100 described above. The discussion of this implementation and the example methods of use are meant to augment the description of the invention above and both should be read together. A method of penetrating and/or removing a blockage in the vasculature can begin with positioning an ultrasonic device 120 having a distal end within a blood vessel. The ultrasonic device 120 can include an ultrasonic transmission member surrounded by a catheter body.

The method continues by advancing the ultrasonic device 120 until the distal end is adjacent to a blockage. The ultrasonic device 120 can be advanced using a monorail or over-the-wire technique, with or without the use of a separate guidewire. In some embodiments, the ultrasonic device 120 is positioned so as to abut the blockage. The blockage may be located in a coronary artery. The ultrasonic device 120 can be visualized or otherwise located using a suitable technique known in the art. For example, the ultrasonic device 120 can include one or more radiopaque markers. The method can continue by transmitting a vibration of greater than or equal to about 18 kHz to the distal end of the ultrasound device 120. In some embodiments, the transmitted vibration is greater than about 40 kHz.

In some embodiments, the vibration that is transmitted through the ultrasound device 120 is pulsed and has a duty cycle. The duty cycle and/or frequency of the duty cycle can be optimized for a particular device and/or particular substrate that the device is likely to encounter. In contrast to the application of a continuously applied constant vibration, the application of a pulsed ultrasonic vibration can cause greater displacement and/or more erratic movement of the distal portion of the ultrasonic device which can increase the device's ability to penetrate hard substances.

In some embodiments, the vibration that is transmitted through the ultrasound device 120 starts at a first frequency and changes to at least a second frequency different than the first frequency. In some embodiments, the applied frequency vibration sweeps through a range of frequencies from a first frequency to a second frequency. The sweep can be a continuous sweep though predetermined ranges of frequencies. In some embodiments, the sweep through a range of frequencies comprises discrete incremental steps up and or down through a range of frequencies. In some embodiments the range of ultrasonic frequencies applied to the device is random and/or discontinuous. In some embodiments the range of frequencies includes at least one resonant frequency of the ultrasonic device.

In some embodiments, the resonant frequency of the device is determined and the system drives the ultrasonic device at or near the resonant frequency of the device. The resonant frequency can be determined prior to or during use of the device. In some embodiments the energy that is transmitted through the device can be paused and a measurement signal can be sent through the device. The measurement signal can be used to determine the actual resonant frequency of the device at that particular point in time. The system can then adjust to drive the device at the actual resonant frequency.

In some embodiments, the system determines the displacement of the distal end of the device. The reflected vibrations can be monitored to help determine the amount of ultrasonic energy that reaches the distal end of the device. The applied vibration can then be adjusted based at least in part on how much energy is reflected. That is to say, if the system determines that a large portion of the applied vibration is being reflected, the system can increase the amplitude of the input wave applied to the device. In this way, the drive can be continuously adjusted to help ensure that enough energy is reaching the distal end of the device. In some embodiments, the displacement of the distal tip is kept relatively constant by adjusting the applied wave form based at least in part on the amount of energy that is reflected.

The method can continue by advancing the distal end 300 of the ultrasound device 120 through the blockage. The ultrasound device 120 can then be removed from the patient. In some embodiments, a stent is placed in the vessel.

Figure 6:
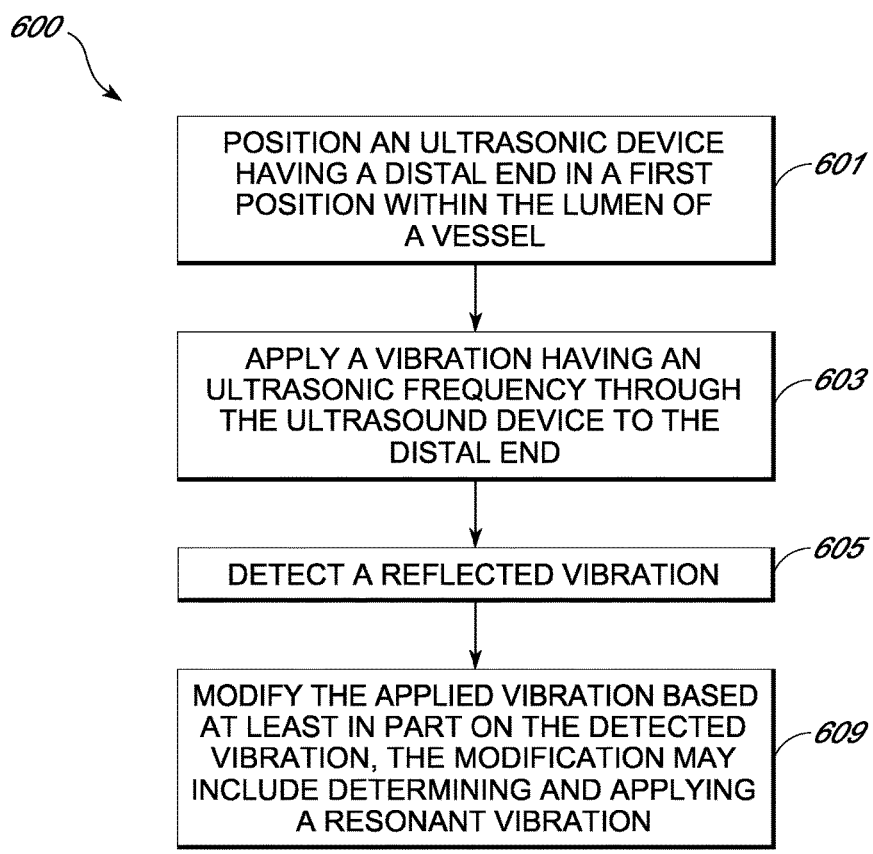

FIG. 6 is a flow diagram illustrating to method 600 of recanalizing a vessel. The method can begin at block 601 by positioning an ultrasonic device having a distal end in a first position within the lumen of the vessel. The vessel may include a partial or total occlusion. The method 600 can continue at block 603 by transmitting ultrasonic vibrations to the distal end of the ultrasonic device. At least one reflected vibration may be detected at block 605. The method can continue at block 609 by modifying the applied vibration(s) at least in part on the detected vibration(s). The detected vibration(s) may be used to determine a resonant frequency of the ultrasonic device. The applied vibration may then be adjusted. In some embodiments, the adjustment comprises applying the resonant frequency that was determined at least in part by the reflected vibration(s). The method can end by advancing the distal end through the vessel to recanalize the vessel.

The various embodiments described above thus provide a number of ways to provide for treatment of occluded vessels. In addition, the techniques described may be broadly applied for use with a variety of medical procedures. Of course, it is to be understood that not necessarily all such objectives or advantages may be achieved in accordance with any particular embodiment using the systems described herein. Thus, for example, those skilled in the art will recognize that the systems may be developed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Although these techniques and devices have been disclosed in the context of certain embodiments and examples, it will be understood by those skilled in the art that these techniques and devices may be extended beyond the specifically disclosed embodiments to other embodiments and/or uses and obvious modifications and equivalents thereof. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein should not be limited by the particular disclosed embodiments described above.

What is claimed is:

1. A therapeutic ultrasonic vibration delivery system comprising:
   an elongate ultrasound transmission device having distal and proximal ends;
   an ultrasonic driver coupled to the proximal end of the transmission device and having a swept driving mode; and
   a detector coupled to the elongate ultrasound transmission device and configured to determine the displacement of the distal end of the elongate ultrasound transmission device; wherein the detector is configured to determine the displacement at least in part by detecting a reflected vibration.

2. The system of claim 1, wherein the swept driving mode continuously sweeps through a range of ultrasonic frequencies.

3. The system of claim 2, wherein the range of ultrasonic frequencies includes at least one resonant frequency of the transmission device.

4. The system of claim 1 further comprising a catheter shaft wherein the transmission device is disposed in the catheter shaft.

5. The system of claim 1 wherein the detector is one or more of a wave detector, a reflected wave detector, a tip displacement detector, a resonant frequency detector, or a wave amplitude detector.

6. A therapeutic ultrasonic vibration delivery system comprising:
   an elongate ultrasound transmission device having a distal end and a proximal end;
   an ultrasonic driver coupled to the proximal end of the transmission device and configured to transmit ultrasonic vibrations through the transmission device; and
   a detector coupled to the transmission device and configured to determine the displacement of the distal end of the transmission device, wherein the detector is configured to determine the displacement at least in part by detecting a reflected vibration.

* * * * *